(12) United States Patent
Rabello et al.

(10) Patent No.: US 8,492,597 B2
(45) Date of Patent: Jul. 23, 2013

(54) PRODUCTION OF PROPYLENE GLYCOL FROM GLYCERINE

(75) Inventors: Carlos René Klotz Rabello, Rio de Janeiro (BR); Marlito Gomes Junior, Rio de Janeiro (BR); Bernardo Galvão Siqueira, Rio de Janeiro (BR); Raphael Bezerra de Menezes, Rio de Janeiro (BR); Wilson Kenzo Huziwara, Rio de Janeiro (BR); Tomas Shinobu Yamada, São Paulo (BR); Lígia Maria Marçareli de Oliveira, Paraná (BR); Giselle de Carvalho Oliveira, Rio de Janeiro (BR); William Victor Carlos Cândido, Paraná (BR)

(73) Assignee: Petroleo Brasileiro S.A.-Petrobras, Rio de Janeiro (BR)

( * ) Notice: Subject to any disclaimer, the term of this patent is extended or adjusted under 35 U.S.C. 154(b) by 175 days.

(21) Appl. No.: 13/034,435

(22) Filed: Feb. 24, 2011

(65) Prior Publication Data
US 2011/0295044 A1    Dec. 1, 2011

(30) Foreign Application Priority Data

Feb. 24, 2010   (BR) ..................................... 1000430

(51) Int. Cl.
*C07C 27/00*    (2006.01)
(52) U.S. Cl.
USPC ........... 568/861; 568/852; 568/862; 568/868; 568/869

(58) Field of Classification Search
None
See application file for complete search history.

(56) References Cited

U.S. PATENT DOCUMENTS

| 2005/0009901 A1 | 1/2005 | Wright et al. |
| 2005/0244312 A1 | 11/2005 | Suppes et al. |
| 2008/0275277 A1 | 11/2008 | Kalagias |

FOREIGN PATENT DOCUMENTS

| WO | 03/035582 A1 | 5/2003 |
| WO | 2007/053705 A2 | 5/2007 |
| WO | 2008/012244 A1 | 1/2008 |
| WO | 2008/049470 A1 | 5/2008 |
| WO | 2008/051540 A2 | 5/2008 |
| WO | 2008/133939 A1 | 11/2008 |
| WO | WO 2008133939 A1 * | 11/2008 |
| WO | WO 2009145691 A1 * | 12/2009 |

* cited by examiner

*Primary Examiner* — Sudhakar Katakam
(74) *Attorney, Agent, or Firm* — Sughrue Mion, PLLC

(57) ABSTRACT

The present invention describes a process for the production of propylene glycol from glycerol, the transformation of purified glycerol to propylene glycol being carried out by means of a reaction of hydrogenolysis, in the liquid phase, where the two stages of the reaction take place simultaneously and in one and the same reactor (1) under specified conditions of temperature and pressure, and the effluent from the fixed-bed reactor (1) is led to subsequent process stages that comprise separation and purification.

3 Claims, 2 Drawing Sheets

PRODUCTION OF PROPYLENE GLYCOL FROM GLYCERINE

FIELD OF THE INVENTION

The present invention relates to processes for the production of propylene glycol from glycerol. Specifically, the invention relates to the production of propylene glycol from glycerol by a reaction of hydrogenolysis.

BACKGROUND OF THE INVENTION

Currently we are seeing a significant increase in supply of glycerol on the market, largely due to worldwide expansion of biodiesel production. In the process of production of biodiesel, glycerol is a by-product generated at a weight ratio of 10/1 (biodiesel/glycerol).

However, this excess in the supply of glycerol has a direct impact on reduction of its commercial value, so that its use in various other applications becomes viable.

Various studies have been initiated with the aim of making use of this surplus glycerol as a raw material for the production of new products.

The number of technical publications on this subject is increasing as solutions are being devised for utilizing this glycerol surplus.

One of the products under investigation that is arousing interest is propylene glycol and its production from glycerol, whatever its origin.

PRIOR ART

From the prior art in this area, we may mention in particular some documents that are representative of the development of processes relating to this subject.

Document WO 2008/051540 A2 (Archer-Daniels-Midland Company) presents a process for the production of propylene glycol from glycerol that uses a fluidized-bed reactor operating at temperatures in the range from 178° C. to 205° C., pressures in the range from 1200 psi to 1600 psi, with hydrogen/glycerol molar ratio in the range from 1:1 to 10:1, and a space velocity in the range from $0.5\ h^{-1}$ to $10\ h^{-1}$. The feed supplied to the reactor is a solution, predominantly aqueous, containing at least 30 wt. % of glycerol in an alkaline medium selected from metal hydroxides, alkoxides, basic salts and metal oxides.

Document WO 2007/053705 A2 (University of Missouri Board of Curators) presents a process for producing a mixture of acetol and propylene glycol in any proportions from glycerol in the vapour phase. The glycerol partial pressure is in the range from 0.01 bar to 0.5 bar and the temperature is in the range from 80° C. to 300° C. The hydrogen partial pressure in the process is in the range from 0.01 bar to 25 bar. A heterogeneous catalyst is used that has at least one element of group I or VIII of the periodic table, ruthenium, copper, chromium, or a combination of these elements.

Documents US 2005/0244312 and PI 0507874-1 (Galen J. Suppes, William Rusty Sutterlin and Mohanprasad Dasari) present processes for the production of acetol, propylene glycol or a mixture of glycerol and propylene glycol, mainly for use as antifreeze, from glycerol as raw material. For the production of propylene glycol, the emphasis is on a process conducted in two stages, the first stage being the production of acetol by reactive distillation, in which the glycerol is dehydrated, obtaining acetol with the aid of a catalyst, the acetol being distilled immediately from the reaction mixture with the aid of a catalyst. This first stage employs reactors in batch or semi-batch mode, a temperature in the range from 170° C. to 270° C., pressure in the range from 0.2 bar to 25 bar, the glycerol for the feed must contain between 0 and 15 wt. % of water, with a heterogeneous catalyst that can have an element selected from palladium, nickel, rhodium, chromium, copper or a combination of these, preferably a catalyst based on a combination of copper and chromium. In a second stage, the acetol produced is mixed with hydrogen and undergoes hydrogenation to propylene glycol with the aid of a catalyst. In this second stage the reaction time is in the range from 0.1 to 24 hours, the temperatures are in the range from 50° C. to 250° C., preferably from 150° C. to 220° C., the pressure is between 1 bar and 25 bar, preferably between 10 bar and 20 bar, the acetol feed contains a maximum of 50 wt. % of water, preferably between 0% and 35%, with a catalyst that can be selected in the same way as for the first stage, a catalyst based on a combination of copper and chromium being preferred.

Document WO 2008/049470 A1 (Clariant International Ltd.) presents an autoclave process for the production of propylene glycol from glycerol, in which said glycerol must have a purity of at least 95%, under hydrogen pressure in the range from 20 bar to 100 bar, at a temperature in the range from 180° C. to 240° C. and in the presence of a catalyst that comprises from 20% to 0% of copper oxide, 30% to 70% of zinc oxide and 1% to 10% of manganese oxide.

Document WO 2007/010299 (Davy Process Technology Ltd.) presents a process for the production of propylene glycol from glycerol, carried out in the vapour phase in the presence of a copper-based catalyst. The process temperature is in the range from 160° C. to 260° C. and the pressure is in the range from 10 bar to 30 bar. The volume ratio of hydrogen to glycerol is between 400:1 and 600:1 with a space velocity between $0.01\ h^{-1}$ and $2.5\ h^{-1}$.

Document WO 2008/012244 (Davy Process Technology Ltd.) presents modifications to the process in the aforementioned document by adding various stages to the process with emphasis on reduction of the amount of hydrogen required for the process when operating in this regime with stages.

Document WO 03/035582 (Battelle Memorial Institute & Michigan State University) presents a process for hydrogenolysis of sugars containing 6 carbon atoms and polyols, including glycerol, using a multi-metal solid catalyst that contains rhenium. The process is conducted at a temperature in the range from 120° C. to 250° C., with a pH of the liquid feed in the range from 8 to 13 and a hydrogen pressure during the hydrogenolysis reaction of the glycerol ranging from 600 psi to 1800 psi.

Document WO 2008/133939 (Archer-Daniels-Midland Company) presents a process of catalytic hydrogenolysis of glycerol in which the space velocity of the feed is in the range from $0.5\ h^{-1}$ to $2.5\ h^{-1}$. The feed is composed of a solution that contains between 25% and 40% of glycerol USP (United States Pharmacopeia), alkalized with hydroxide or alkoxide of sodium or potassium so that a pH is obtained in the range from 6 to 14. The hydrogen pressure is between 500 psi and 2000 psi, at a temperature in the range from 150° C. to 300° C. and a hydrogen/glycerol molar ratio in the range from 1:1 to 10:1.

The document emphasizes that, besides producing propylene glycol as main compound, there is formation of butanediols and a proportion of other diols in the range from 0.04% to 2.31%.

The section for purification/separation of products proposed in this process comprises a stage of removal of the alkalizing agent by means of an ion exchange resin and by stages of distillation of the products. In the first distillation column, water and light alcohols are removed at the top and are sent to a second distillation column to be separated. The effluent from the bottom of the first distillation column goes to a plurality of small distillation columns, in which the residual water and unconverted glycerol are separated. The stream enriched with propylene glycol is led to a distillation column for separation of other by-products, principally ethylene glycol.

Document US 2008/0275277 A1 (Peter Kalagias) presents a process for purification of propylene glycol and ethylene glycol, produced from a renewable source. The process uses a polar solvent to aid separation by distillation of the components of the mixture. In this process, a mixture of polyols produced in hydrogenolysis of the renewable raw material, including glycerol, is mixed with a polar solvent that does not form an azeotrope with the components of the mixture, and is then distilled. This type of distillation, called extractive distillation, is used when components of a mixture have a relatively low volatility, reducing the chances of efficient separation by conventional distillation. The polar solvent that is added interacts in different ways with the components of the mixture, causing a change in the relative volatility of the components, thus making it possible to separate them.

It has been observed that investigations are continuing, although the processes mentioned above are observed to have very little preoccupation with the stage of separation of the products.

The present invention presents an alternative route for obtaining propylene glycol, with refinement of the process as a whole; as well as recovery, separation and final treatment of the products obtained.

SUMMARY OF THE INVENTION

The present invention relates to a process for the production of propylene glycol from glycerol, in which the reactions take place in the liquid phase and the glycerol used as raw material is, specifically, the by-product from the process for obtaining biodiesel.

The glycerol obtained from biodiesel, called crude glycerol, is produced with a purity in the range from 40% to 85%. For it to be used as a raw material for the production of propylene glycol according to the present invention, it must be purified by means of purification processes normally employed in the industry, giving a glycerol with a degree of purity in the range from 90 to 99.9 wt. %.

The transformation of this purified glycerol to propylene glycol is effected by means of a reaction of hydrogenolysis, which is conducted in the liquid phase, with the two stages of the reaction taking place simultaneously and in one and the same reactor.

In the first stage the glycerol, under the action of temperature and a catalyst, is transformed to acetol and water. In the second stage the acetol, under the action of a catalyst and hydrogen gas, is transformed to propylene glycol.

The recycle gas is led to a methanation reactor, for converting the CO and $CO_2$ impurities present in the hydrogen recycle stream to methane, for subsequent recycling to the reactor, minimizing the effects of catalyst deactivation and maintaining glycerol conversion above 95% and selectivity of propylene glycol above 90%.

The effluent from the reactor is led to a section for separation and purification, after which a final product is obtained with high purity and low content of impurities.

DETAILED DESCRIPTION OF THE INVENTION

The present invention relates to a process for the production of propylene glycol from glycerol of any origin, in which the reactions take place in the liquid phase.

The glycerol stream can come from biodiesel units, soapworks or production of fatty acids.

For purposes of illustration, the glycerol that will be referred to hereinafter originates from the process for obtaining biodiesel, where it is generated as a by-product.

The glycerol obtained in the course of the process for production of biodiesel initially has a degree of purity in the range from 40% to 85% due to the presence of numerous reaction by-products, for example:

salts containing sodium, chlorine, sulphur and phosphorus, which deactivate the catalyst irreversibly;

fatty acids, phospholipids, glycerides, soaps and biodiesel residues, which deactivate the catalyst by blocking the pores.

The production of propylene glycol has this glycerol as raw material. However, before it is admitted to the hydrogenolysis reactor, the glycerol is first submitted to a stage of concentration and a stage of purification, for removing impurities such as: salts and non-glycerol organic material (NGOM), resulting in a glycerol stream with a degree of purity normally situated in a range of values between 90% w/w and 100% w/w. The process most commonly used for the purification stage is vacuum fractional distillation.

Figure 1:
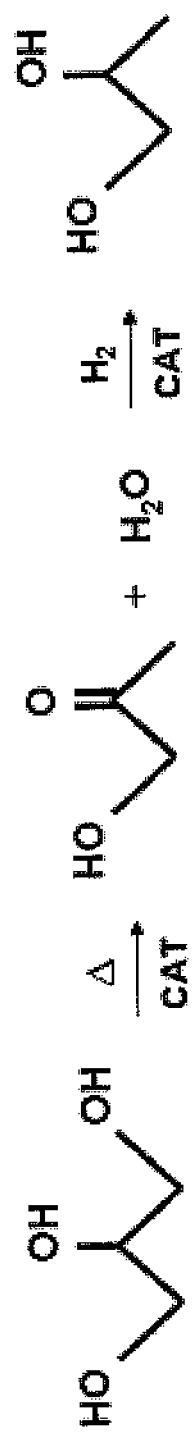
FIG. 1 shows the chemical equations illustrating the transformation of glycerol from biodiesel to propylene glycol.

After being purified, the glycerol is transformed to propylene glycol by means of a reaction of hydrogenolysis. This reaction is carried out in the liquid phase, in which the two stages of reaction take place simultaneously and in one and the same reactor, i.e. the glycerol, under the action of temperature and a catalyst, is transformed to acetol and water and then, under the action of a catalyst and hydrogen gas, the acetol is transformed to propylene glycol. The chemical reactions involved in the process are shown in FIG. 1.

Figure 2:
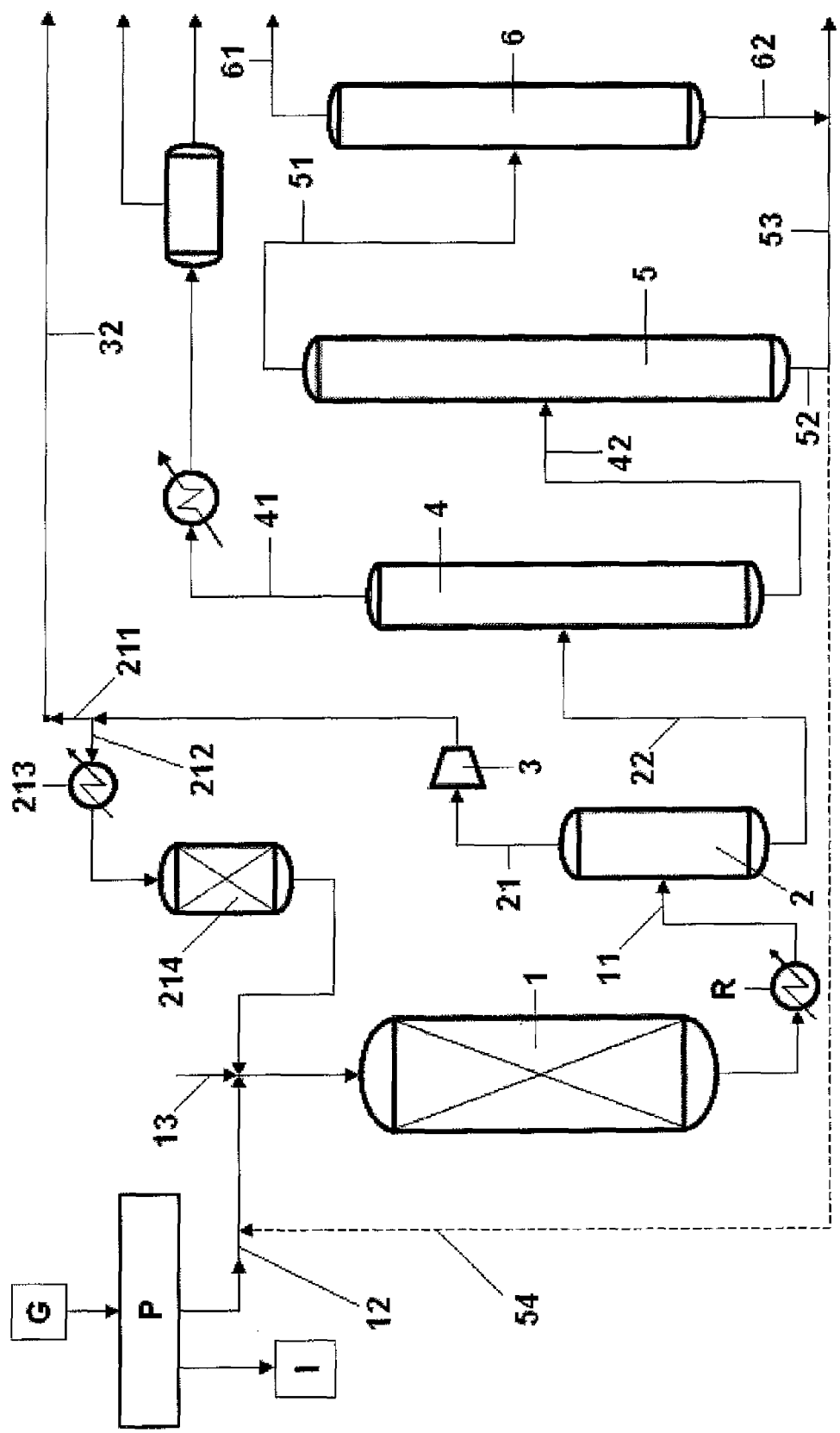
FIG. 2 shows a simplified flowsheet of the process of hydrogenolysis of glycerol for obtaining propylene glycol.

The process for the production of propylene glycol from glycerol obtained from biodiesel, according to the present invention, can be described referring to FIG. 2. Basically, it comprises the following steps:

a) submitting the glycerol (G), received from biodiesel production, containing impurities, to a stage of purification (P) for removing the impurities (I) by any known purification process, provided said process supplies a glycerol with a degree of purity in the range from 90 to 99.9 wt. %;

b) proceeding to the reaction of hydrogenolysis, in a fixed-bed adiabatic reactor (1) operating in descending flow, in the liquid phase, where the two stages of reaction take place simultaneously as follows:

activating a catalyst based on copper chromite by passing hydrogen through it;

pressurizing the fixed-bed reactor (1) to a pressure that can be in the range from 5 $kgf/cm^2$ to 50 $kgf/cm^2$;

raising the temperature of the catalyst bed to a working temperature that is in the range from 160° C. to 260° C.;

starting admission of purified glycerol with a certain water content via a feed line (12) and starting admission of hydrogen via a gas line (13), with a molar ratio of glycerol to hydrogen in the range from 10 mol/mol to 120 mol/mol and a space velocity in the range from 0.1 h$^{-1}$ to 10 h$^{-1}$ with respect to the limiting reactant (glycerol);
c) cooling by means of a cooler (R) and withdrawing the effluent preferably from the bottom of this reactor and conveying it via a reacted product line (11);
d) sending the effluent from the fixed-bed reactor (1) via the reacted product line (11) to a phase separating vessel (2), to remove a stream containing hydrogen and non-condensable light compounds by means of a first top stream (21), and removal of liquid effluent by means of a first bottom stream (22);
e) sending the first top stream (21) received from the phase separating vessel (2) to a recycling compressor (3), which compresses the contents of this stream, where a first portion (211) is conveyed via a first purge line (32) intended for burning by incineration;
f) sending a second portion (212) of the first top stream (21) received from the phase separating vessel (2) to a heater (213), and then to a methanation reactor (214) for transformation of contaminating compounds CO and $CO_2$ present in the first top stream (21) to methane, then to be mixed in the feed line (12) and recycled to the hydrogenolysis reactor (1);
g) sending the liquid effluent from the first bottom stream (22) received from the phase separating vessel (2) to a primary fractionating tower (4), which discharges, via a second top stream (41), water and light polar compounds such as methanol, ethanol, n-propanol and isopropanol, while the bottom effluent is conveyed via a second bottom stream (42);
h) sending the bottom effluent of the second bottom stream (42) received from the primary fractionating tower (4) to a tower for removing heavy fractions (5), which removes unreacted glycerol and other heavy products formed during the hydrogenolysis reaction, which are conveyed via a third bottom stream (52) to destinations that can be selected from: a second burning line (53) for incineration and power generation and a second recycling line (54) where glycerol is returned to the fixed-bed reactor (1), while propylene glycol containing impurities is conveyed via the third top stream (51);
i) sending the effluent of the third top stream (51) received from the tower for removing heavy fractions (5) to a purification tower (6), which removes impurities such as ethylene glycol, 1,3-propylene glycol and a small content of heavy compounds, which are conveyed via a fourth bottom stream (62) as far as the junction with the second burning line (53) for incineration and power generation, while propylene glycol with a high degree of purity is withdrawn by means of the fourth top stream (61).

The methanation reactor (214) employs a nickel-based catalyst supported on alumina, operates in a temperature range between 200° C. and 450° C., at pressure in the range from 5 kgf/cm$^2$ to 50 kgf/cm$^2$, and a space velocity in the range from 5000 h$^{-1}$ to 20 000 h$^{-1}$.

The CO and $CO_2$ are converted to methane in the methanation reactor (214) according to the following reactions (1) and (2):

$$CO + 3H_2 \rightarrow CH_4 + H_2O \quad (1)$$

$$CO_2 + 4H_2 \rightarrow CH_4 + 2H_2O \quad (2)$$

Both CO and $CO_2$ act as reversible poisons for the catalyst, being adsorbed on the metal sites and reducing their hydrogenating function, temporarily. Because of this, the conversion and selectivity of the catalyst are gradually reduced and heavy compounds are deposited on the surface of the catalyst, through condensation of the glycerol that was not converted.

At the same time, other benefits may be obtained:
a) lower consumption of glycerol: greater selectivity and productivity;
b) lower consumption of hydrogen: reduction of the purge;
c) operation at lower temperatures;
d) longer catalyst campaign;
e) reduction in size of the process equipment;
f) reduction of operating cost;
g) reduction of the amount of liquid and gaseous effluents;
h) increase in operating time of the unit.

Owing to the exothermic nature of the reactions involved, the fixed-bed reactor (1) can contain more than one catalyst bed and have a cooling system between the beds. The propylene glycol produced according to the present invention has an estimated degree of purity above 99% with low content of impurities.

Two examples of application of the process according to the present invention will be presented below, purely for purposes of illustration.

EXAMPLE 1

After activation in situ of the catalyst, by passing hydrogen through it, the system was pressurized to approximately 20 kgf/cm$^2$ with hydrogen and the working temperature was adjusted to 225° C.

Purified glycerol and hydrogen in a glycerol/hydrogen molar ratio of 1/120 were admitted at a temperature of 225° C. with a space velocity of 0.5 h$^{-1}$ with respect to the limiting reactant, glycerol, into the fixed-bed adiabatic reactor (1) containing 557 mL of catalyst. The fixed-bed reactor (1) operates with a temperature gradient of 10° C. Analysis showed that the effluent from the reactor (1) had a conversion of glycerol of about 99% and the selectivity for propylene glycol was 89.8%.

EXAMPLE 2

The same reaction system as in EXAMPLE 1 was supplemented with a methanation reactor (214) as the means for removing CO and $CO_2$ formed in the process. The operating conditions were maintained, initially constant and equal to EXAMPLE 1.

Once complete conversion of the glycerol was observed, the temperature was reduced to 220° C., to give a content of 0.2% of glycerol in the final product.

It was observed that with the introduction of the aforesaid system for reducing impurities, the catalyst displayed greater activity and selectivity in comparison with the results in EXAMPLE 1.

The full composition of the effluent from the reactor in each of the two examples can be compared with the aid of the following Table 1:

TABLE 1

| COMPONENT | FORMULA | Example 1 T = 225° C. | Example 2 T = 220° C. |
|---|---|---|---|
| Methanol | C2H6O | 0.1% | 0.08% |
| Ethanol | C3H8 | 0.2% | 0.06% |
| Ethylene glycol | C2H6O2 | 0.2% | 0.01% |
| n-Propanol | C3H8O | 0.8% | 0.98% |
| Isopropanol | C3H8O | 0.1% | 0.73% |
| Acetol | C3H6O2 | 2.3% | 1.66% |

TABLE 1-continued

| COMPONENT | FORMULA | Example 1 T = 225° C. | Example 2 T = 220° C. |
|---|---|---|---|
| Propanoic acid | C3H6O2 | 0.2% | 0.01% |
| 1,2-Propylene glycol | C3H8O2 | 89.8% | 93.52% |
| 1,3-Propanediol | C3H8O2 | 0.1% | 0.01% |
| 2,4-Dimethyl-2-hydroxy-methyl-1,3-dioxolane | C6H12O4 | 0.9% | 0.70% |
| 2-Methyl-2,4-dihydroxy-methyl-1,3-dioxolane | C6H12O3 | 1.8% | 0.71% |

Although the invention has been described in its preferred embodiment, the main concept that guides the present invention, which is a process for the production of propylene glycol from glycerol, in particular from glycerol from biodiesel, is preserved with respect to its innovative character, where a person skilled in the art will be able to envisage and implement variations, modifications, changes, adaptations and the like, conceivable and compatible with the working means in question, but without departing from the scope and spirit of the present invention, which are represented by the following claims.

The invention claimed is:

1. A method for producing propylene glycol from glycerol comprising the following steps:
   a) submitting the glycerol (G) received from biodiesel production and with impurities to a stage of purification (P) for removing the impurities (I) by a purification process, provided said process supplies a glycerol with a degree of purity in the range from 90 to 99.9 wt. %;
   b) proceeding to the reaction of hydrogenolysis, in a fixed-bed adiabatic reactor (1) operating in descending flow, in the liquid phase, where the two stages of the reaction take place simultaneously as follows:
   activating a catalyst based on copper chromite by passing hydrogen through it;
   pressurizing the fixed-bed reactor (1) to a pressure that can be in the range from 5 kgf/cm$^2$ to 50 kgf/cm$^2$;
   raising the temperature of the catalyst bed to a working temperature that is in the range from 160° C. to 260° C.;
   starting admission of purified glycerol with a known water content via a feed line (12) and starting admission of hydrogen via a gas line (13), with a molar ratio of glycerol to hydrogen in the range from 10 mol/mol to 120 mol/mol and a space velocity in the range from 0.1 h$^{-1}$ to 10 h$^{-1}$ with respect to the limiting reactant (glycerol);
   c) cooling by means of a cooler (R) and withdrawing the effluent preferably from the bottom of this reactor and conveying it via a reacted product line (11);
   d) sending the effluent from the fixed-bed reactor (1) via the reacted product line (11) to a phase separating vessel (2), to remove a stream containing hydrogen and non-condensable light compounds by means of a first top stream (21), and removal of the liquid effluent by means of a first bottom stream (22);
   e) sending the first top stream (21) received from the phase separating vessel (2) to a recycling compressor (3), which compresses the contents of this stream where a first portion (211) is conveyed via a first purge line (32) for burning by incineration;
   f) sending the liquid effluent from the first bottom stream (22) received from the phase separating vessel (2) to a primary fractionating tower (4), which discharges, via a second top stream (41), water and light polar compounds such as methanol, ethanol, n-propanol and isopropanol, while the bottom effluent is conveyed via a second bottom stream (42);
   g) sending the bottom effluent of the second bottom stream (42) received from the primary fractionating tower (4) to a tower for removing heavy fractions (5), which removes unreacted glycerol and other heavy products formed during the hydrogenolysis reaction, which are conveyed via a third bottom stream (52) to destinations that can be selected from a second burning line (53) for incineration and power generation and a second recycling line (54) where unreacted glycerol is returned to the fixed-bed reactor (1), while propylene glycol with impurities is conveyed via the third top stream (51);
   h) sending the effluent of the third top stream (51) received from the tower for removing heavy fractions (5) to a purification tower (6), which removes impurities such as ethylene glycol, 1,3-propylene glycol and a small content of heavy compounds, which are conveyed via a fourth bottom stream (62) as far as the junction with the second burning line (53) for incineration and power generation, while propylene glycol with a degree of purity of at least about 99 wt. % is withdrawn by means of the fourth top stream (61);
   characterized in that a second portion (212) of the first top stream (21) received from the phase separating vessel (2) is sent to a heater (213), and then goes into a methanation reactor (214) for transformation of contaminating compounds CO and CO$_2$ present in the first top stream (21) to methane, then to be mixed in the feed line (12) and recycled to the hydrogenolysis reactor (1).

2. The method for production of propylene glycol from glycerol according to claim 1, wherein the methanation reactor employs a nickel-based catalyst supported on alumina, operates in a temperature range between 200° C. and 450° C., at pressure in the range from 5 kgf/cm$^2$ to 50 kgf/cm$^2$, and a space velocity in the range from 5000 h$^{-1}$ to 20000 h$^{-1}$.

3. The method for production of propylene glycol from glycerol according to claim 1, wherein a conversion of glycerol above 95% and selectivity for propylene glycol greater than 90% are achieved.

* * * * *